United States Patent [19]

Cerutti et al.

[11] Patent Number: 5,750,334
[45] Date of Patent: May 12, 1998

[54] DETECTION OF HUMAN PAPILLOMAVIRUS MRNA IN CERVICAL SMEARS

[75] Inventors: Peter Cerutti, Pully; Jeannette Whitcomb, Epalinges; Jacob Zijlstra, Coppet, all of Switzerland; Ethel-Michelle de Villiers, Hirschberg, Germany

[73] Assignee: Behring Diagnostics GmbH, Marburg, Germany

[21] Appl. No.: 479,567

[22] Filed: Jun. 7, 1995

Related U.S. Application Data

[63] Continuation of Ser. No. 191,705, Feb. 4, 1994, abandoned, which is a continuation of Ser. No. 929,506, Aug. 18, 1992, abandoned, which is a continuation of Ser. No. 433,899, Nov. 9, 1989, abandoned.

[30] Foreign Application Priority Data

Nov. 11, 1988 [DE] Germany .................. 38 38 269.5

[51] Int. Cl.⁶ .................. C12Q 1/70; C12Q 1/68; C12P 19/34
[52] U.S. Cl. .................. 435/5; 435/6; 435/91.2; 935/77; 935/78
[58] Field of Search .................. 435/5, 6, 91.2; 935/77, 78; 536/24.33

[56] References Cited

U.S. PATENT DOCUMENTS 4,983,728  1/1991  Herzog et al. .................. 536/27

FOREIGN PATENT DOCUMENTS 237 362   9/1997  European Pat. Off. .
WO 88/06634  9/1988  WIPO .

OTHER PUBLICATIONS

D.K. Shibata, et al., "Detection of Human Papilloma Virus In Paraffin–Embedded Tissue Using The Polymerase Chain Reaction," J. Exp. Med., vol. 167, pp. 225–230, Jan. 1988.

D. Smotkin, et al., "Transcription of human papillomavirus type 16 early genes in a cervical cancer and a cancer–derived cell line and identification of the E7 protein," Proc. Natl. Acad. Sci. USA, vol. 83, pp. 4680–4684, Jul. 1986.

D.J. McCance, "News on Papillomaviruses," Nature, vol. 335, pp. 765–766, Oct. 27, 1988.

European Patent Application No. 237 362 A1, H.A. Erlich, et al., "Process For Detecting Specific Nucleotide Variations And Genetic Polymorphisms Present In Nucleic Acid and Kits Therefor," published Sep. 16, 1987.

European Patent Application No. 256 321 A1, T. Oltersdorf, et al., "Expressionsprodukte des menschilchen Papillomavirus Type 18, fur diese Proteine spezifische Antikorper und diese Antikorper bzw, entsprechende DNA enthaltende Diagnostika," published Feb. 24, 1988.

E. Schwarz, et al., "Structure and Transcription of Human Papillomavirus Sequences in Cervical Carcinoma Cells," Nature, vol. 314, pp. 111–114, Mar. 7, 1985.

R.K. Saiki et al., Science 239:487–491 (1988).

A. Schneider–Gadicke et al., Cancer Res. 48:2969–2974 (1988).

DBA abstract, Doc. No:88–04189, Nature, (1988) 331,6155 pp. 461–462.

Koos et al., Mol. Endocrinol 3(12), 1989, 2041–2048, Biosis Abstract No. 89069393.

Dallas et al., J. Med. Virol. 27/2, 1989, 105–111, EMBASE Abstract No. 89078758.

Melchers et al., J. Clin. Microbiol., 27/8, 1989, 1711–1714, DBA Abstract Accession No. 89–11163.

Cole et al., J.Mol.Biol. 193:599–608 (1987).

Schneider–Gadicke et al., EMBO J. 5(9):2285–2292 (1986).

Maniatis et al., Cold Spring Harbor Lab., N.Y. (1982) pp. 264–265.

Singleton et al., John Wiley & Sons (1978, 1987) p. 567.

*Primary Examiner*—Stephanie W. Zitomer
*Attorney, Agent, or Firm*—Finnegan, Henderson, Farabow, Garrett & Dunner, L.L.P.

[57] ABSTRACT

The invention relates to the direct detection of human papillomavirus MRNA and DNA. The recently developed polymerase chain reaction was modified in order to improve the sensitivity and specificity. By choosing appropriate oligonucleotide primers (amplimers) and reaction temperatures, individual HPV genes from among the total cell DNA can be identified and amplified to an extent such that non-isotopic detection is possible. In addition, use of reverse transcription permits selective amplification of spliced mRNA and thus permits indication of premalignant or malignant conditions and/or lesions.

4 Claims, 2 Drawing Sheets

3.4 kb 1.6 kb 4.5 kb 2.3 kb 1.5 kb

5,750,334

DETECTION OF HUMAN PAPILLOMAVIRUS MRNA IN CERVICAL SMEARS

This application is a continuation of application Ser. No. 08/191,705, filed Feb. 4, 1994, which is a continuation of application Ser. No. 07/929,506, filed Aug. 18, 1992, which is a continuation of 07/433,899, filed Nov. 9, 1989, all now abandoned.

The invention relates to the direct detection of human papillomavirus DNA. This entailed the recently developed polymerase chain reaction (PCR; Saiki et al. (1988) Science 239, 487–491) being modified in order to improve the sensitivity and specificity. By choosing appropriate oligonucleotide primers (amplimers) and reaction temperatures, individual HPV genes from among the total cell DNA can be identified and amplified to an extent such that non-isotopic detection is possible. In addition, use of reverse transcription permits selective amplification of spliced mRNA and thus permits indication of pre-malignant or malignant conditions and/or lesions.

There is a strong correlation between the occurrence of cervical carcinomas and the detection of HPV serotypes 16, 18, 31 and 33 in cervical tissue. Admittedly, the related HPV serotypes 6 and 11 are also frequently present in the genital tract, but these are associated with benign lesions, genital warts and condylomata. The genome of HPV 16 and 18 possesses 8 open reading frames (ORF; FIG. 1). L-1 and L-2 code for structural protein whereas the significance of the other ORFs is not quite as well understood. There is a strong connection between E6/E7 regions integrated into the host genome and the transformation to malignancy. It was shown for the E7 ORF that it codes for a cytoplasmic phosphoprotein present in large quantities in HPV-infected cells. The role played by this protein in transformation and maintenance of malignancy is not known. The E6/E7 regions are strongly transcribed in transformed cells. Both a transcript of the entire E6/E7 region and spliced RNAs exist. The splicing pattern which is similar in HPV 16 and 18 leads to a translation product called E6*. (Schneider-Gädicke et al. (1988) Cancer Res. 48, 2969–2974). This splicing pattern probably correlates with the malignant potential of the HPV viruses which is displayed by HPV 16, 18, 31 and 33 but which HPV 6 and 11 do not have. The spliced mRNA transcript, which is shifted in the reading frame, for HPV 16 and HPV 18 E6* is diagrammatically shown in FIG. 2 and FIG. 3. An even smaller spliced mRNA of approximately 1.5 kb found for HPV 16 is shown in addition. The methods hitherto available for detection of the virus, for example in situ DNA hybridization with radio-labelled DNA probes, are difficult to carry out, time-consuming and frequently insufficiently sensitive. The polymerase chain reaction method (PCR; Saiki et al, loc cit.) used for amplification of HPV DNA was also unsuitable as a routine method.

We have found that the polymerase chain reaction method can be simplified for the detection of HPV and that HPV can be detected in cervical smears after about 3 hours when suitable amplimers and concentrations of dimethyl sulfoxide appropriate thereto are used. The polymerase used was Taq polymerase, and temperatures of 89° C. and 63° C. at cycle times of 1 minute were chosen. If a cDNA synthesis step by means of reverse transcriptase is carried out beforehand the presence of spliced mRNA to E6* can be established from the occurring DNA bands (FIG. 4 and FIG. 5) and the presence of pre-malignant or malignant lesions can be shown to be probable.

SUMMARY OF THE INVENTION

The invention thus relates to:

a) a simplified PCR method for the detection of HPV by choosing suitable conditions such as amplimer sequences, reaction temperatures (preferably 89° C. and 63° C.), increased concentrations of amplimers and deoxynucleotide triphosphates, short cycle times of 1 to 2 minutes, and starting the PCR at a temperature at which double-stranded DNA is still "molten" so that the specificity is considerably improved, b) where a suitable choice of amplimers permits the simultaneous detection of several types of viruses (e.g. HPV 16, 18, 31 and 33), and DNA fragments of characteristic length are obtained for each individual virus and are quantified by densitometry after separation by agarose gel electrophoresis and staining with ethidium bromide, c) a step for reverse transcription of mRNA preceding the amplification reactions, in order to establish the presence of E6* by way of detection of amplified spliced MRNA, the amplimers chosen being preferably those which span the splice sites when the presence of E6* is to be tested for, d) coamplification of a single-copy gene (such as the human IL-2 receptor, β-globin or c-H-ras gene), for internal standardization and for checking that the amplification reactions have functioned satisfactorily.

In case (c) amplimers of 14–20 nucleotides can be chosen which span the splice site approximately symmetrically, if only amplification products of the reverse transcriptase reaction are to be obtained. The amplimer ACAGAGGTGC, the arrow marking the splice site, is an example. However, the E6* RNA is also detected by its different fragment length, as described in the examples with the amplimer pairs 24/26 and 21/22 for HPV 18 and HPV 16, respectively. The method described above using the example of E6* of HPV 18 and HPV 16 is generally applicable for the detection of spliced mRNA by choice of suitable amplimers.

The invention is further described in the following examples and patent claims.

EXAMPLE 1

Figure 1:
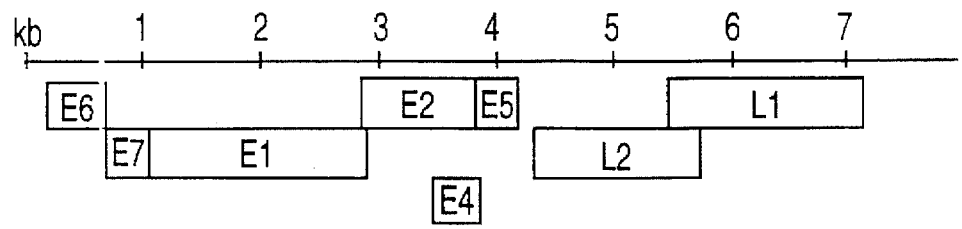
FIG. 1: Open reading frames of HPV 18 (HPV 16 has similar structure).
Figure 2A:
FIG. 2: Graphic representation of the E6/E7 region of HPV 18
 a) DNA organization
 b) E6/E7 mRNA of 3.4 kb
 c) spliced mRNA for E6* of 1.6 kb.
Figure 2B:
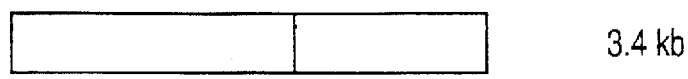
Figure 2C:
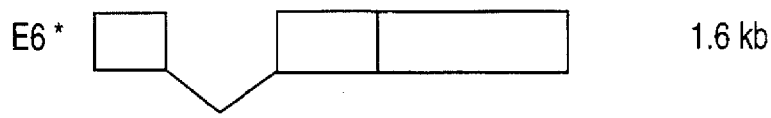
Figure 3A:
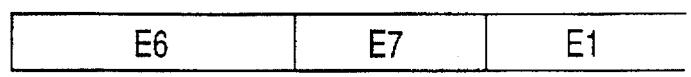
FIG. 3: Graphic representation of the E6/E7 region of HPV 16
 a) DNA organization
 b) E6/E7 mRNA of 4.5 kb
 c) spliced MRNA for E6* of 2.3 kb
 d) smaller spliced mRNA of about 1.5 kb.
Figure 3B:
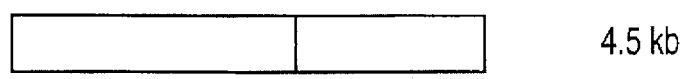
Figure 3C:
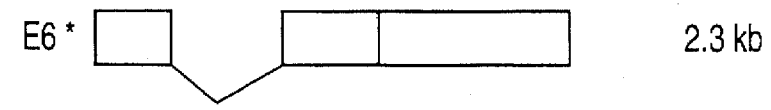
Figure 3D:
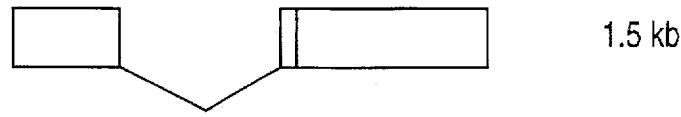
Figure 4A:
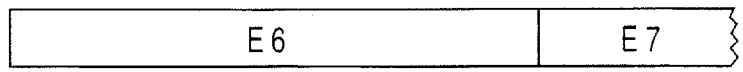
FIG. 4: Amplimer positions and splice sites in amplified HPV 18 DNA segments
 a) E6/E7 portion of the HPV 18 genome
 b) position of the amplimers 24, 25 and 26
 c) size of the amplified DNA fragment or of unprocessed mRNA
 d) Size of the amplified CDNA of the spliced E6* RNA.
Figure 4B:
Figure 4C:
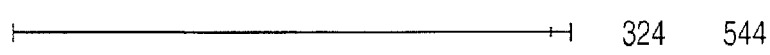
Figure 4D:
Figure 5A:
FIG. 5: Amplimer positions and splice sites in amplified segments of HPV 16 DNA
 a) E6/E7 portion of HPV 16 genome b) position of amplimers 21, 22 and 23
c) size of the amplified DNA fragment or of the un-processed mRNA
d) size of the amplified CDNA of the spliced E6* RNA
e) size of the smaller MRNA band identified by Smotkin and Wettstein, Proc. Natl. Acad. Sci (USA) 83, 4680 (1986).
Figure 5B:
Figure 5C:
Figure 5D:
Figure 5E:
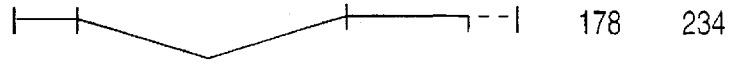

Removal of Clinical Specimens for the Detection of HPV DNA and/or for the Detection of E6* RNA After application of the cervical smear for the histological examination ("pap smear") the usual wooden spatula containing the residual material was immersed in 20 ml of ice-cold Earle's BSS glucose (0.2 g/l $CaCl_2$, 0.4 g/l KCL, 0.2 g/l $MgSO_4$, $7H_2O$, 6.8 g/l NaCl, 2.2 g/l $NaHCO_3$, 0.14 g/l $NaH_2PO_4$, $H_2O$, 1 g/l glucose). After a maximum of 5 hours on ice the sample was shaken manually and the spatula removed. The sample was centrifuged at 4° C./100×g, during which the mucus floats to the top while the cells are deposited at the bottom of the tube. The supernatant was decanted and the cell residue washed once with phosphate-buffered saline. The cell residue was frozen at −70° C. and kept in the frozen state until processed further.

EXAMPLE 2

Reverse Transcription

A reaction mixture having a total volume of 5 µl has the following composition:

| Buffer A (10 ×) | 0.5 µl |
|---|---|
| 10 × BSA | 0.5 µl |
| Nucleoside triphosphates (NTPs, 5 mM) | 1.0 µl |
| RNasin | 0.25 µl |
| Dithiothreitol | 0.25 µl |
| Amplimer (primer) | 0.5 µl |
| Reverse transcriptase | 0.5 µl |
| $H_2O$ | 0.5 µl |
| Cell sample | 0.1 µl |

Buffer A (10 x) has the following composition:
500 mM Tris HCl pH 8.3
70 mM $MgCl_2$
500 mM KCl
100 mM β-mercaptoethanol
10×BSA contains 1.70 mg/ml BS A in $H_2O$
RNasin (promega) contains 40 U/µl
Dithiothreitol is 20 mM Amplimers are contained in $H_2O$ in a concentration of 400 µg/ml. Reverse transcriptase (Boehringer Mannheim) contains 20–25 U/µl.

The reaction mixture, without addition of the cell sample, was mixed and 4 µl portions were pipetted into Eppendorf tubes; 1 µl portions of the cell sample to be tested were then added. A 200 µl layer of liquid paraffin was then placed on top, the mixture was sonicated at setting 2 with a B15 Bronson sonicator for 15 seconds, and the emulsion was separated in an Eppendorf bench centrifuge at room temperature. Finally this was followed by incubation at 42° C. for 10 minutes with the reaction subsequently stopped by heating to 89° C.

EXAMPLE 3

Amplification

A reaction mixture is formed of 20 µl of amplification mixture and 5 µl of reaction mixture from the reverse transcription reaction or appropriately buffered cell sample, the amplification mixture having the following composition:

| Buffer B (10 ×) | 2 µl |
|---|---|
| 10 × BSA | 2 µl |
| Deoxynucleotide triphosphate (dNTPs, 25 mM) | 1 µl |
| Amplimer | 0.5 µl |
| Taq polymerase | 0.4 µl |
| $H_2O$ | 14.3 µl |

Buffer B (10 x) has the following composition
70 mM $Mgcl_2$
500 mM KCl
100 mM β-mercaptoethanol The Taq polymerase (Biores) has 5 U/µl (for other constituents see Example 2).

20 µl of amplification mixture equilibrated at 89° C. was then added to 5 µl of sample which was also incubated at 89° C. The DNA amplification was then carried out in 1-minute cycle steps at 89° C./63° C., 25 to 40 cycles as a rule being sufficient for detection of HPV DNA or mRNA in up to at least 20 cells.

EXAMPLE 4a

Selection of Amplimers for HPV 18

| | | |
|---|---|---|
| 1 | ATTAATACTT TTAACAATTG TAGTATATAA AAAAGGGAGT AACCGAAAAC | |
| 51 | GGTCGGGACC GAAAACGGTG TATATAAAAG ATGTGAGAAA CACACCACAA | |
| 101 | TACTATGGCG CGCTTTGAGG ATCCAACACG GCGACCCTAC AAGCTACCTG | E6 |
| 151 | ATCTGTGCAC GGAACTGAAC ACTTCACTGC AAGACATAGA AATAACCTGT | |
| 201 | GTATATTGCA AGACAGTATT GGAACTTACA GAGGTATTTG AATTTGCATT | |
| 251 | TAAAGATTTA TTTGTCGTGT ATAGAGACAG TATACCCCAT GCTGCATGCC | |
| 301 | ATAAATGTAT AGATTTTTAT TCTAGAATTA GAGAATTAAG ACATTATTCA | |
| 351 | GACTCTGTGT ATGGAGACAC ATTGGAAAAA CTAACTAACA CTGGGTTATA | |
| 401 | CAATTTATTA ATAAGGTGCC TGCGGTGCCA GAAACCGTTG AATCCAGCAG | |
| 451 | AAAAACTTAG ACACCTTAAT GAAAAACGAC GATTTCACAA CATAGCTGGG | |
| 501 | CACTATAGAG GCCAGTGCCA TTCGTGCTGC AACCGAGCAC GACAGGAACG | |

```
551  ACTCCAACGA CGCAGAGAAA CACAAGTATA ATATTAAGTA TGCATGGACC  E7
601  TAAGGCAACA TTGCAAGACA TTGTATTGCA TTTAGAGCCC CAAAATGAAA
651  TTCCGGTTGA CCTTCTATGT CACGAGCAAT TAAGCGACTC AGAGGAAGAA
701  AACGATGAAA TAGATGGAGT TAATCATCAA CATTTACCAG CCCGACGAGC
751  CGAACCACAA CGTCACACAA TGTTGTGTAT GTGTTGTAAG TGTGAAGCCA
801  GAATTGAGCT AGTAGTAGAA AGCTCAGCAG ACGACCTTCG AGCATTCCAG
851  CAGCTGTTTC TGAACACCCT GTCCTTTGTG TGTCCGTGGT GTGCATCCCA
901  GCAGTAAGCA ACAATGGCTG ATCCAGAAGG TACAGACGGG GAGGGCACGG
951  GTTGTAACGG CTGGTTTTAT GTACAAGCTA TTGTAGACAA AAAAACAGGA
```

Amplimer positions are underlined.
E6* splice sequences are dotted and underlined.
Amplimer sequences:
No. 24 (position 167–186)
AGT GAA TTC TTC GAA CAC TTC ACT GCA AGA CA
No. 26 (position 667–686)
AGT GAA TTC GCG CGC TTA ATT GCT CGT GAC AT
No. 25 (position 647–666)
AGT GAA TTC TCT AGA AGG TCA ACC GGA ATT TC The 4 "leader" triplets are EcoRI-cleavable oligonucleotide linkers.

An intron is present between position 236 and 417 (182 bp), so that a band of 544 bp is detectable on amplification of DNA with the No. 24/No. 26 amplimer pair.

On amplification of RNA, that is after a preceding step with reverse transcription of the spliced mRNA, an additional band of 362 bp is detected.

EXAMPLE 4b

Selection of Amplimers for HPV 16

```
  1  ACTACAATAA TTCATGTATA AAACTAAGGG CCTAACCCAA ATCCGTTGAA
 51  CCGAAACCGG TTAGTATAAA AGCACACATT TTATGCACCA AAAGAGAACT
101  GCAATGTTTC AGGACCCACA GGAGCCACCC AGAAAGTTAC CACAGTTATG  E6
151  CACAGAGCTG CAAACAACTA TACATGATAT AATATTACAA TGTGTGTACT
201  GCAAGCAACA GTTACTGCCA CGTGAGGTAT ATGACTTTGC TTTTCGGGAT
251  TTATGCATAG TATATAGAGA TGGGAATCCA TATGCTGTAT GTCATAAATG
301  TTTAAAGTTT TATTCTAAAA TTAGTGAGTA TAGACATTAT TGTTATAGTT
351  TGTATGGAAC AACATTAGAA CAGCAATACA ACAAACCGTT GTGTGATTTG
401  TTAATTAGGT GTATTAACTG TCAAAAGCCA CTGTGTCCTG AAGAAAAGCA
451  AAGACATCTG GACAAAAAGC AAAGATTCCA TAATATAAGG GGTCGGTGGA
501  CCCGTCGATG TATGTCTTGT TGCAGATCAT CAAGAACACG TAGAGAAACC
551  CAGCTGTAAT CATGCATCGA GATACACCTA CATTGCATGA ATATATGTTA  E7
601  GATTTGCAAC CAGAGACAAC TGATCTCTAC TGTTATGAGC AATTAAATGA
651  CAGCTCAGAG CAGGAGGATG AAATAGATGG TCCAGCTGGA CAAGCAGAAC
701  CGGACAGAGC CCATTACAAT ATTGTAACCT TTTGTTGCAA GTGTGACTCT
751  ACGCTTCGGT TGTGCGTACA AAGCACACAC GTAGACATTC GTACTTTGGA
801  AGACCTGTTA ATGGGCACAC TAGGAATTGT GTGCCCCATC TGTTCTCAGA
851  AACCATAATC TACCATGGCT GATCCTGCAG GTACCAATCG GGAAGAGGGT
901  ACGGGATGTA ATGGATGGTT TTATGTAGAG GCTGTAGTGG AAAAAAAAAC
951  AGGGGATGCT ATATCAGATG ACGAGAACGA AAATGACAGT GATACAGGTG
```

Amplimer positions are underlined.
E6* splice sequences are dotted and underlined.
Amplimer sequences:
No. 21 (position 198–207)
AGT GAA TTC AGT ACT GCA AGC AAC AGT TAC TG
No. 22 (position 601–620)

AGT GAA TTC AAC GTT GTC TCT GGT TGC AAA TC

No. 23 (position 658–677)

AGT GAA TTC AGA TCT ATT TCA TCC TCC TCC TC

The 4 "leader" triplets are each EcoRI-cleavable oligonucleotide linkers.

The introns are present at about position 225 to 410 (186 bp) and 254 to 524 (270 bp). A band of 447 bp is detectable on amplification of DNA with the No. 21/No. 22 amplimer pair, and additional bands of about 261 and 177 bp are detected on amplification of RNA. that is after a preceding step with reverse transcription of spliced mRNA.

We claim:

1. A method for the direct detection of spliced human papillomavirus (HPV) mRNA in a cervical smear sample which comprises:
   (a) combining the sample with reverse transcriptase in a reaction mixture and sonicating to release mRNA;
   (b) synthesizing a cDNA by means of reverse transcription to establish the presence of E6 spliced MRNA;
   (c) amplifying said cDNA in a polymerase chain reaction (PCR) by using:
      i) deoxynucleotide triphosphate concentrations above 0.2 mM,
      ii) amplimer concentrations above 0.5 µM, wherein said amplimers span the E6 splice sequence of the spliced MRNA to be detected, and
      iii) cycle times of 1 to 2 minutes at two temperatures of 70° C.–95° C. and 50° C.–70° C., wherein the PCR is started above the melting temperature; and
   (d) detecting said amplified cDNA, wherein said correspondent cDNA is distinguished from other amplified fragments by its size.

2. The method as claimed in claim 1, wherein said two temperatures are 89° C. and 63° C.

3. The method as claimed in claim 1, wherein the PCR is carried out with addition during step (b) of up to 20% v/v dimethyl sulfoxide.

4. The method as claimed in claim 2, wherein the PCR is carried out with addition during step (c) of up to 20% v/v dimethyl sulfoxide.

* * * * *